United States Patent
Harris

Patent Number: 5,853,376
Date of Patent: Dec. 29, 1998

[54] UROGENITAL MUSCLE EXERCISER

[76] Inventor: Howard T. Harris, 2235 Whiteback, Houston, Tex. 77084

[21] Appl. No.: 672,556

[22] Filed: Jun. 28, 1996

Related U.S. Application Data

[63] Continuation-in-part of Ser. No. 329,665, Oct. 26, 1994, Pat. No. 5,531,226, which is a continuation-in-part of Ser. No. 917,786, Jul. 20, 1992, abandoned, which is a continuation-in-part of Ser. No. 683,558, Apr. 10, 1991, abandoned.

[51] Int. Cl.⁶ .................................................. A61B 5/00
[52] U.S. Cl. ............................................................ 600/587
[58] Field of Search ................................... 600/587, 591, 600/593, 595, 546

[56] References Cited

U.S. PATENT DOCUMENTS

| | | | |
|---|---|---|---|
| 4,256,118 | 3/1981 | Nagel | 128/733 |
| 4,258,720 | 3/1981 | Flowers | 128/694 |
| 4,709,704 | 12/1987 | Lukesiewicz | 128/644 |
| 4,729,377 | 3/1988 | Granek et al. | 128/639 |
| 4,909,263 | 3/1990 | Norris | 128/788 |
| 4,913,162 | 4/1990 | Leary et al. | 128/774 |
| 4,949,729 | 8/1990 | Haski | 128/774 |
| 4,989,615 | 2/1991 | Hochberg | 128/774 |

*Primary Examiner*—Max Hindenburg

[57] ABSTRACT

A urogenital muscle exercise system is located totally external to a body to aid in the exercising of urogenital muscles.

The device consists of:
- a sensor means located totally external to the body to detect urogenital muscle activity, or the urogenital muscle status or change of status of said body,
- a communication means for said sensor means to communicate to a feedback means, detected urogenital muscle activity, or the urogenital muscle status or change of status,
- a feedback means to indicate to a user of the urogenital muscle exercise system, urogenital muscle activity, or the urogenital muscle status or change of status, detected by said sensor means,
- and a holding means for holding said sensor means in position to detect urogenital muscle activity, or the urogenital muscle status or change of status.

A sensor means detects urogenital muscle activity, or the urogenital muscle status or change of status, and then communicates what it detects to a feedback means. The feedback means then indicates to a user of the urogenital muscle exercise system, the urogenital muscle activity, or the urogenital muscle status or change of status detected.

8 Claims, 1 Drawing Sheet

UROGENITAL MUSCLE EXERCISER

This is a Continuation-In-Part of a Continuation-In-Part application, Ser. No. 08/329,665, filed on 26 Oct. 1994 now U.S. Pat. No. 5,531,226; which is a Continuation-In-Part of Continuation-In-Part application Ser. No. 07/917,786, filed on 20 Jul. 1992 now abandoned; which is a Continuation-In-Part application of the Parent application Ser. No. 07/683,558, filed on 10 Apr. 1991 now abandoned.

BACKGROUND

1. Field of Invention

This invention relates to the urogenital muscles, specifically to devices which are more safe and have improved methods of aiding in the exercising of the urogenital muscles. This is done with feedback indicating urogenital muscle activity, or status or change of status. There is nothing to insert into the body. Fully functioning prototypes already exist.

2. Discussion of Prior Art

Heretofore, the urogenital muscle exercisers have had some sort of probe that has to be inserted into the body. When the female uses the probe, the probe has to be inserted into her vagina. Some of these devices can be used by a male inserting the probe up his rectum. Examples of prior art are U.S. Pat. No. 2,507,858 and U.S. Pat. No. 2,541,520 both to Kegel, U.S. Pat. No. 3,640,284 to De Langis, U.S. Pat. No. 3,752,150 to Harris, U.S. Pat. No. 4,050,449 to the assignee of Medical Products Development Corporation, and U.S. Pat. No. 4,989,615 to Hochberg.

The following prior arts were disclosed in the Parent Application:

U.S. Pat. No. 2,507,858 to Kegel,
U.S. Pat. No. 2,541,520 to Kegel,
U.S. Pat. No. 3,640,284 to De Langis,
U.S. Pat. No. 3,752,150 to Harris,
U.S. Pat. No. 4,050,449 assigned to Medical Products Development Corporation.

The P.T.O. earlier found the following prior arts:

U.S. Pat. No. 4,256,118 to Nagel,
U.S. Pat. No. 4,258,720 to Flowers,
U.S. Pat. No. 4,709,704 to Lukasiewicz,
U.S. Pat. No. 4,729,377 to Granek et al.,
U.S. Pat. No. 4,909,263 to Norris,
U.S. Pat. No. 4,913,162 to Leang et al.,
U.S. Pat. No. 4,949,729 to Haski,
U.S. Pat. No. 4,989,615 to Hochberg.

Some disadvantages of the prior art, which are caused by the probe that must be inserted into the body are;

one has phallic fear or masturbatory guilt,
the prior art is harder to use,
the probe has to be meticulously cleaned between uses.

SUMMARY—OBJECTS AND ADVANTAGES

Some advantages of this invention over the prior art are;
there is no probe to meticulously clean between each use,
one does not have any phallic fear or masturbatory guilt using this invention, because there is not anything inserted into one's body.

Some of the benefits of having strong urogenital muscles are that it helps;

the individual to have greater sexual satisfaction,
the individual to have better bladder control,
the female to have an easier and safer time of delivery while giving birth to her child, because she will have more control when to and when not to push the baby out of her vagina during delivery,
some women to overcome symptoms of P.M.S.

One object of this invention is to provide a device that can be used by either a male or female, with feedback being provided that indicates urogenital muscle activity, or the urogenital muscle status or change of status.

Still another object of this invention is to provide an EASIER device for urogenital muscle exercises to be done with.

Still another object of this invention is to provide a SAFER device for urogenital muscle exercises to be done with. This invention is safer than the other urogenital exercise inventions because there are no injuries that can happen as a result of using a probe that has to be placed inside the body.

Still another object of this invention is to provide a way to do urogenital exercises with more comfort. This is because there is no part of the device that is placed into the body.

Still another object of this invention is to provide a means for isometric exercises.

Still another object of this invention is to provide an apparatus of this type that is well suited otherwise to its intended function.

SOME EXAMPLES OF EMBODIMENTS

This invention works on the basis that urogenital muscle activity inside the body can be detected not only from inside the body, but also from outside of the body. This urogenital muscle activity can be detected by a device that is placed against, or near, the external part of the urogenital area of the body. This can be done with NOTHING being placed in the body. The sensor for this device can be of any type which can detect this urogenital muscle activity, or the urogenital muscle status or change of status. Some examples for the sensors used are:

A bladder-like means containing pressure.

A bladder-like means containing pressure, which has a self-resilient means to cause the said bladder-like means to resiliently go back to its initial shape.

A resistance-like means in which the shape or position of the resistance-like means effects the resistance amount. Skin movement, or skin bulges, will cause a change in the shape or position of the resistance-like means. A change in the shape or position of the resistance-like means will cause a change in resistance amount. The status of the resistance amount is used to detect the urogenital muscle activity, or the urogenital muscle status or change of status.

A capacitance-like means, in which the skin movement, or skin bulges, will cause a change in the distance between the plates of the capacitance-like means. This will cause a change in the amount of capacitance. The status of the capacitance amount is used to detect the urogenital muscle activity, or the urogenital muscle status or change of status.

An inductance-like means, in which the skin movement, or skin bulges, will cause a change in the shape of the inductance-like means. This will cause a change in the relationship among the coils of the inductance-like means with one another. The said change in relationship will cause a change in the amount of inductance. The status of the inductance amount is used to detect the urogenital muscle activity, or the urogenital muscle status or change of status.

A switch-like means, in which the skin movement, or skin bulges, will cause the switch-like means to close, or partially close, or to open, or partially open. The status of the switch-like means being open or closed, or partially open, or partially closed, is used to detect the urogenital muscle activity, or the urogenital muscle status or change of status.

An electrode means to sense urogenital muscle activity, or the urogenital muscle status or change of status.

If a bladder-like means is used as a sensor to detect urogenital muscle activity or status or change of status, there is an advantage over Hochberg's U.S. Pat. No. 4,989,615 in that this bladder-like means can be made so that there is self-resiliency with NO need for a resilient-insert element. As a result, there is nothing inside the bladder-like means that could move around or otherwise cause trouble with the functioning of the device. Thus, there is an omission of an element. Self-resiliency of the said bladder-like means can be gained by making the walls of the bladder-like means out of, or coated with, a rubber-like material or other material with resilient characteristics.

The invention consists of a urogenital muscle exercise system located totally external to the body to aid in the exercising of urogenital muscles.

This invention can also be used for isometric exercises.

The drawings provided are for the purpose of explanation. The drawings should not be construed as limitations on the scope of the invention.

The examples given on how to make such a device is for the purpose of explanation. The examples given should not be construed as limitations on the scope of the invention.

The device consists of:

a sensor means LOCATED TOTALLY EXTERNAL to the body to detect urogenital muscle activity, or the urogenital muscle status or change of status of the said body, a communication means for said sensor means to communicate to a feedback means, detected urogenital muscle activity, or the urogenital muscle status or change of status, a feedback means to indicate to a user of the urogenital muscle exercise system, the urogenital muscle activity, or urogenital muscle status or change of status, detected by said sensor means, and a holding means for holding said sensor means in position to detect urogenital muscle activity, or the urogenital muscle status or change of status.

Figure 1:
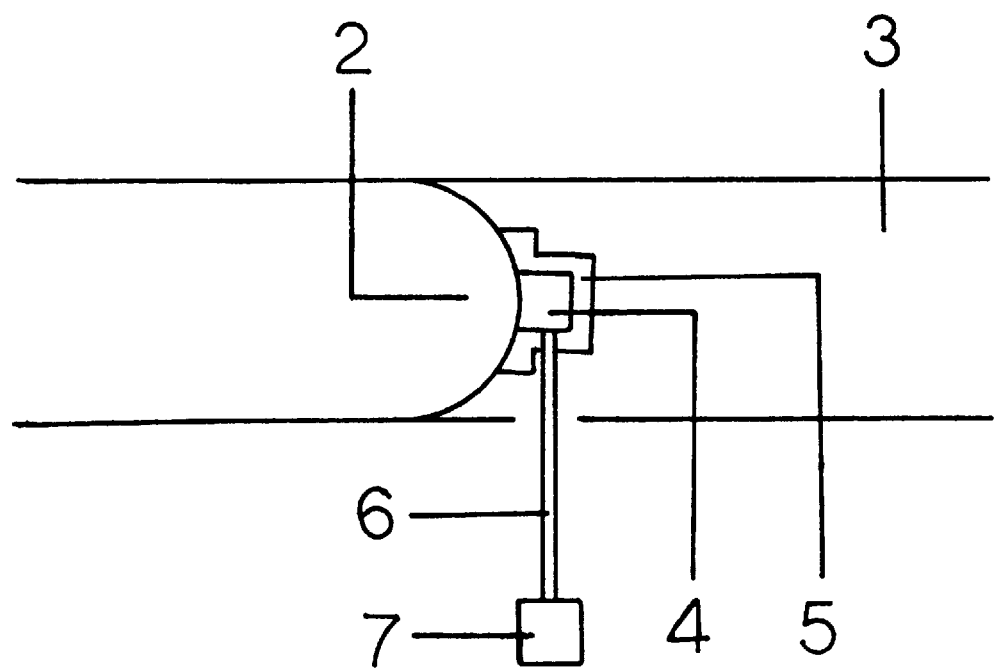
FIG. 1 shows only one of the many ways in which the urogenital muscle exercise system can be made and placed in position for usage. This figure is for explanation purposes only. This figure is not to be construed as any limitation on the scope of the invention. This invention is NOT limited to humans.

Item number 2 represents part of the external urogenital area of a human body.

Item number 3 represents a human leg on the other side of a urogenital muscle exercise system.

Item number 4 represents a sensor means LOCATED TOTALLY EXTERNAL to a body to detect urogenital muscle activity, or the urogenital muscle status or change of status.

Item number 5 represents one way in which a holding means can hold a sensor means in position to detect urogenital muscle activity, or urogenital muscle status or change of status. One method can be for the holding means to be a sticking means to cause the sensor means to stick to the urogenital area of the body. The holding means can be other than a sticking means. The sticking means is only an example of how this can be done.

Item number 6 represents one method in which a communication means is used for a sensor means to communicate to a feedback means, the urogenital muscle activity, or urogenital muscle status or change of status detected. One method can be for the communication means to be a wiring means. There are ways other than a wiring means in which this can be done. The wiring means is only an example of how this can be done.

Item number 7 represents one way in which a feedback means can be used to indicate to a user of a urogenital muscle exercise system, the urogenital muscle activity, or urogenital muscle status or change of status, detected by the sensor means. One method for the feedback means can be a digital readout. The feedback means can be other than a digital readout. The digital readout is only an example of how this can be done.

CONCLUSION, RAMIFICATIONS, AND SCOPE OF THE INVENTION

Thus the reader will see that this invention can be safely used by the normal layman individual, and there is NOT any part of this invention that is inserted into the body in any manner.

This invention can be used as a means for isometric exercises.

While my above description contains specificities, these should NOT be construed as limitations on the scope of the invention, but rather as explanations of ways a device of this invention can be made. Many other variations are possible.

Accordingly, the scope of this Continuation-In-Part should be determined NOT by the examples illustrated, but ONLY by the claims and their equivalents.

The scopes of all Continuations-In-Part of this invention together determine the scope of this invention.

What is claimed is:

1. A urogenital muscle exercise system LOCATED TOTALLY EXTERNAL to the body to provide muscular feedback comprising:

a sensor means to detect urogenital muscle activity, or the urogenital muscle status or change of status, a holding means for holding said sensor means in position to detect urogenital muscle activity, or the urogenital muscle status or change of status, a communications means for said sensor means to communicate to a feedback means, the detected urogenital muscle activity, or the urogenital muscle status or change of status, and a feedback means to indicate to a user of the urogenital muscle exercise system, the detected urogenital muscle activity, or the urogenital muscle status or change of status.

2. A urogenital muscle exercise system as claimed in claim 1 wherein said sensor means includes a bladder-like means containing pressure.

3. A urogenital muscle exercise system as claimed in claim 2 wherein said bladder-like means includes a self-resilient means which causes said bladder-like means to resiliently go back to its initial shape.

4. A urogenital muscle exercise system as claimed in claim 1 wherein said sensor means includes a resistance-like means in which the shape or position of the resistance-like means effects the resistance amount, and the status of the resistance amount is used to detect the urogenital muscle activity, or the urogenital muscle status or change of status.

5. A urogenital muscle exercise system as claimed in claim 1 wherein said sensor means includes a capacitance-like means in which the status of the capacitance amount is used to indicate the detected urogenital muscle activity, or the urogenital muscle status or change of status.

6. A urogenital muscle exercise system as claimed in claim 1 wherein said sensor means includes an inductance-like means in which the status of the inductance amount is used to indicate urogenital muscle activity, or the urogenital muscle status or change of status.

7. A urogenital muscle exercise system as claimed in claim 1 wherein said sensor means includes a switch-like means:
   whose status of being open or closed is used to indicate the amount of urogenital muscle activity, or the urogenital muscle status or change of status,
   or the degree to which the said switch-like means is partially open or partially closed is used to indicate the amount of urogenital muscle activity, or the urogenital muscle status or change of status.

8. A urogenital muscle exercise system as claimed in claim 1 wherein said sensor means includes an electrode means to sense urogenital muscle activity, or the urogenital muscle status or change of status.

* * * * *